United States Patent [19]

Higgins et al.

[11] 4,318,784
[45] Mar. 9, 1982

[54] ENZYMATIC PROCESSES

[75] Inventors: Irving J. Higgins, Wingham; Hugh A. O. Hill, Oxford, both of England

[73] Assignee: National Research Development Corporation, London, England

[21] Appl. No.: 192,504

[22] PCT Filed: Aug. 10, 1979

[86] PCT No.: PCT/GB79/00139

§ 371 Date: Apr. 15, 1980

§ 102(e) Date: Apr. 15, 1980

[87] PCT Pub. No.: WO80/00453

PCT Pub. Date: Mar. 20, 1980

[30] Foreign Application Priority Data

Aug. 15, 1978 [GB] United Kingdom ............... 33388/78

[51] Int. Cl.$^3$ ............................................. C25B 3/04
[52] U.S. Cl. .................................... 204/73 R; 204/72
[58] Field of Search ............................... 204/72, 73 R

[56] References Cited

PUBLICATIONS

A publication by Eddowes and Hill, entitled "Novel Method for the Investigation of the Electrochemistry of Metalloproteins: Cytochrome C", published in J.C.S. Chem. Comm. 1977, pp. 771-772.

A publication by Coughlin, Aizawa and Charles, entitled "Preparation and Properties of soluble-insoluble nicotinamide coenzymes" published in Biotechnology and Bioengineering, vol. XVIII, pp. 1999-2208 (1976).

A publication by Aizawa, Coughlin and Charles, entitled "Electro-Regeneration of the Reduced from the Oxidised Form Immobilised NAD", published in Biotechnology and Bioengineering, vol. XVIII pp. 209-215 (1976).

A publication by Coughlin, Aizawa, Alexander and Charles entitled "Immobilised-Enzyme Continous--Flow Reactor incorporating Continuous Electrochemical Regeneration of NAD", published in Biotechnology and Bioengineering vol. XVII pp. 515-526 (1975).

A publication by Aizawa, Coughlin and Charles, entitled "Electrochemical Regeneration of Nicotinamide Adenine Dinucleotide", published in Biochemica et Biophysica Acta 385 (1975) 362-370.

A publication by Aizawa, Suzuki and Kubo, entitled "Electrolytic Regeneration of NADH from NAD+ with a liquid crystal membrane Electrolyde", published in Biochemica et Biophysica Acta, 444 (1976) 886-892.

An English translation of a publication by Fujihira and Osa, entitled "Chemically Modified Electrodes—Crossroads of Biochemistry and Electrochemistry" published in Denki Kgaku—vol. 45, No. 5, 270-280 (1977).

A publication by Landrum, Salmon & Hawkridge, entitled "A Surface-Modified Gold Minigrid Electrode which Heterogeneously reduces Spinnage Ferredoxin" published in Journal of the American Chemical Society, 99:9, Apr. 1977, pp. 3154-3158.

Yeh et al., "Reversible Electrode Reaction of Cytochrome c"; Chemistry Letters, 1977, pp. 1145-1148.

Suzuki et al., "Ethanol and Lactic Acid Sensors Using Electrodes Coated with Dehydrogenase-Collagen Membrane" Bull. of Chem. Soc. of Japan, vol. 48 (11), 3246-3249 (1975).

Schmakel et al., "Nicotinamide Adenine Dinucleotide (NAD+) and Related Compounds, Electrochemical Redox Pattern and Allied Chemical Behavior", Journal of American Chemical Society, 97:18, Sep. 3, 1975.

Scheller et al., "Electrochemical Aspects of Cytochrome P-450 System from Liver Microsomes", Bioelectrochemistry and Bioenergetics 4, 500-507 (1977).

Varfolomeev et al., "Bioelectrocatalysis, Hydrogenase as Catalyst of Electrochemical Hydrogen Ionization", Bioelectrochemistry and Bioenergetics 4, 314-326 (1977).

Kwee et al., "Indirect Electrochemical Reduction of Proteins", Bioelectrochemistry and Bioenergetics 2, 231-244 (1975).

Scheller et al., "Peroxidatic Activity of Liver Microsomal Cytochrome P-450", FEBS Letters vol. 71, No. 2, Dec. 1976, pp. 309-312.

Weibel et al., "Biochemical Fuel Cells—Demonstration of an Obligatory Pathway Involving an External Circuit for the Enzymatically Catalyzed Aerobic Oxidation of Glucose", Archives of Biochemistry and Biophysics 169, 146-151 (1975).

*Primary Examiner*—R. L. Andrews
*Attorney, Agent, or Firm*—Oblon, Fisher, Spivak, McClelland & Maier

[57] ABSTRACT

There are provided processes for carrying out enzymatic reactions, especially processes for the oxidative or reductive transformation of organic compounds catalyzed by enzymes, in which the enzymes require a continuing supply of reducing equivalents to regenerate reduced enzyme species in enzymatically active form, and in which the reducing equivalents are derived electrochemically, including electrochemically from molecular hydrogen, the reducing equivalents preferably being passed directly to the enzyme from the cathode of an electrochemical system.

13 Claims, No Drawings

ENZYMATIC PROCESSES

This invention relates to enzymatic processes, in particular to processes for the oxidative or reductive transformation of organic compounds utilising redox enzymes.

Redox enzymes such as external mono-oxygenases catalyse a wide range of oxidation and reduction reactions in biological systems, many of which are potentially of great industrial importance. In order to accomplish their enzymatic functions, however, these enzymes require a continuing supply of reducing equivalents, normally in the form of electrons, which, in biological systems, are supplied to the enzyme by biologically active electron donor materials, such as NAD and cytochromes. In nature these donor materials undergo continuous regeneration in interactions associated with the main enzyme reaction, but industrial applications of these enzymes would not normally permit this regeneration to take place and thus a continuing supply of fresh donor material would be required to drive the enzyme reaction.

In recent years the electrochemical regeneration of NAD in enzymatically active form has been investigated with a view to coupling this regeneration with enzymatic reactions in which NAD interacts with a substrate material. For example, electrochemical regeneration of the oxidised form of NAD has been coupled with alcohol dehydrogenation catalysed by alcohol dehydrogenase immobilised on alumina (Coughlin et al. Biotechnology and Bioengineering (1975) Vol. XVII, pages 515-526) in a reaction in which free $NAD^+$ is electrochemically regenerated and acts as a hydrogen acceptor converting the alcohol to an aldehyde. The alcohol dehydrogenase of this reaction acts as a site for interaction of the $NAD^+$ and the alcohol, and does not itself undergo chemical change during the reaction to provide an enzymically active reduced enzyme species.

Additionally, however, it is highly likely that NAD will be continually lost by decomposition or otherwise and it will be necessary to "top out" the system with fresh NAD from time to time. Electron donor materials, such as NAD and cytochromes are highly costly, complex, unstable chemicals, some comprising protein components and thus their use as reagents in industrial processes is not at present practical.

It has now been discovered that enzyme reactions which proceed by way of a reduced enzyme species may be carried out without need for biochemical regeneration of electron donor materials and preferably also without the need for a continued supply of fresh donor material either to replace spent material or, in a particularly preferred embodiment, even to "top up" the system.

Accordingly the present invention comprises a process for carrying out an enzymatic reaction which requires a continuing supply of reducing equivalents to regenerate a reduced enzyme species in enzymatically active form, in which the reducing equivalents are derived electrochemically.

Suitable enzymes are characteristically those which are capable of accepting electrons to produce a reduced enzyme species which generally corresponds to the enzymatically active form of the enzyme. Thus the enzymes typically comprise at least one electron receptor component which is an integral part of the enzyme molecule or system. For instance, the enzyme may comprise a single identifiable molecular species which contains either a metal atom which is directly reduced, or a small molecular prosthetic group permanently bound to the enzyme, such as a flavo protein or pteridine, or a normally free species e.g. NAD, which is bound by the enzyme and whilst bound is reduced and acts as the electron receptor. Also, however, the enzyme may comprise a multi-protein complex, in which case there is at least one species within the complex, such as ferredoxin, rubredoxin or a cytochrome e.g cytochrome P450, which acts as an electron receptor and supplies the reducing electrons to the reactive species in the enzyme complex, often by way of a chain of intermediate proteins.

The enzymes which may be used in the process of the present invention are typically redox enzymes including external mono-oxygenases, oxidoreductases, dehydrogenases, hydrogenases, nitrogenases, dioxygenases an luciferases. Often the enzymatic reactions of the invention are those which involve incorporation of molecular oxygen to provide an enzyme/substrate/molecular oxygen complex during reaction. Specific examples of suitable enzymes and enzymatic reactions utilising these enzymes will be apparent to workers skilled in the art.

Typically, however, the processes of the invention are processes for the oxidative or reductive transformation of organic compounds in which the transformation is catalysed by an enzyme and the enzyme requires a continuing supply of reducing equivalents to regenerate a reduced enzyme species in enzymatically active form, and in which the reducing equivalents are derived electrochemically. The organic compounds which may be transformed by the processes of the invention are compounds which characteristically comprise hydrocarbon material and may also comprise functional groups, such as hydroxyl, carbonyl and other groups, and the transformations which may be carried out may be transformations of the hydrocarbon material and/or functional groups attached thereto. It will be appreciated that many of such transformations are potentially of great industrial importance. For example, enzymes and enzymatic processes for effecting transformation of organic compounds to which the present invention may be applied include:

1. External Mono-Oxygenases (i) Microbial higher alkane mono-oxygenases of both of cytochrome P-450 and rubredoxin classes including oxygenases of alkanes e.g. n-octane, alicyclic hydrocarbons, and related systems especially terpenes.

(ii) Microsomal cytochrome $P_{450}$ enzymes from eukaryotic organisms, including systems involved in prostaglandin synthesis, $\omega$-hydroxylation of fatty acids, fatty acid desaturation, cyclization of squalene, steroid interconversions and bile acid metabolism.

(iii) Microbial flavin mono-oxygenases such as $p$-hydroxybenzoate, salicylate, orcinol and melilotate mono-oxygenases.

(iv) NADH-linked methane mono-oxygenases, for instance the systems isolated from *Methylococcus capsulatus* or *Methylosinus trichosporium* which show a very broad substrate specificity, e.g. as described by Higgins et al., Society of General Microbiology Quarterly, 6, 71 (1979) and Biochemical Biophysical Research Communications (1979) (in press), and by Stirling et al., Biochem. J., 177, (1979) 361-364.

(v) Mono-oxygenases which catalyse ring-insertion reactions e.g. cyclohexanone mono-oxygenase.

(vi) O-Demethylases.

(vii) Phenylalanine, tyrosine and tryptophan hydroxylases.
2. Oxidoreductases e.g. ethanol, methanol, lactate, fumarate, succinate oxidoreductases (i.e. including NAD-, flavin- and pteridine-linked enzymes).
3. Dehydrogenases e.g. pyruvate and 2-oxo-glutarate dehydrogenases.
4. Nitrogenase.
5. Dioxygenases that require a reducing agent e.g. bacterial benzene and toluene oxygenases.
6. Luciferases that require a reducing agent.
7. Hydrogenases.

The electrochemically derived reducing equivalents i.e. electrons, may be passed indirectly to the enzyme by means of a suitable carrier. The carrier may comprise a naturally occurring biological carrier such as those biologically active electron donor materials e.g. ferredoxin, pteridine, NAD(P)H, flavins, rubredoxin or free cytochromes, which are associated with the function of enzymes in biological systems. Alternatively the carrier may comprise an artificial carrier, such as quinone, viologen dye, glutathione or ascorbic acid. Preferably, however, the electrochemically derived reducing equivalents are passed directly to the enzyme from the cathode of the electro-chemical system and are used and taken up by the electron receptor component e.g. flavoprotein or cytochrome component of the enzyme. Such direct electrochemical reduction of the enzyme advantageously avoids the use of a carrier material which may comprise an undesirably expensive and chemically unstable material which requires periodic replacement because of loss due to decomposition or otherwise. Thus in the method of the present invention a carrier or preferably the enzyme itself is continuously reduced electrochemically to drive in enzymatic reaction.

In order to successfully continue transfer of electrons to the carrier or the enzyme, the choice of electrodes and electrochemical cell used as well as careful control of the electrochemical conditions employed have been found to be of importance. For example, material which is inert to the biologically active material which it is desired to reduce electrochemically is generally used for the working electrode e.g. gold, platinum, carbon or mercury, and the auxiliary electrode, which may be any suitable material, e.g. graphite, is separated from the working electrode, for instance by an electrically conducting membrane. As regards the electrochemical conditions employed, it is of primary importance to ensure that electron transfer to the carrier or enzyme is not rendered ineffective e.g. by the carrier or enzyme undergoing chemical change, or decomposition or by becoming absorbed at the working electrode i.e. cathode. This may be achieved by use of a liqud crystal coated, semi-conductor or hanging mercury drop working electrode and/or by use of an electron transfer promoter in the electrolyte. Suitable promoters include 4,4'-bipyridyl, and 1,2-(bis-4,4'-bipyridyl) ethylene and similar conjugated and/or heterocyclic chemicals.

Furthermore, it has been found to be desirable to control the potential of the working electrode at or close to the redox potential of the enzyme or carrier species which it is desired to reduce electrochemically. Such control of the potential of the working electrode advantageously permits selective reduction of the desired enzyme or carrier species, for instance, even when the desired enzyme is present in a complex mixture, such as a crude cell extract. The redox potentials of each enzyme or carrier species are typically distinctive of the species. For example, the redox potential of the mono-oxygenase enzyme system of *Methylosinus trichosporium* has been found to be approximately $-0.1$ v versus the potential of the normal hydrogen electrode. The desired redox potentials may be determined empirically in each case by methods well known in the electrochemical art.

In order to facilitate control of the working electrode at the desired redox potential, a third electrode is typically included within the electrochemical cell. For instance, a reference electrode, such as a standard calomel reference electrode, is used, preferably located within the working region of the cell especially in close proximity to the working electrode. Any suitable means may be used to control the potential of the working electrode, such as, for example a potentiostat.

In the processes of the invention the enzyme is introduced into the working compartment of a suitable electrochemical cell, electrochemically derived reducing equivalents are supplied to the enzyme, and substrate is supplied to the system and products recovered as desired. Generally regeneration of the enzyme and transformation of the organic compound substrate material takes place simultaneously, for instance in a homogeneous system. The enzyme may be in purified form, although this is not normally necessary as choice of preferred operating potential advantageously permits selective electrochemical regeneration of the enzyme e.g. as a component of a crude cell extract. The enzyme may be present in the electrolyte in the free state, or, in preferred embodiments for use in industrial applications, the enzyme may be immobilised, for instance, on or with a suitable solid phase material e.g. polysaccharide gel beads or absorbed or carbon particles. Also immobilised enzyme may be used advantageously in flow-through reactor systems, in which substrate may be flowed through the reactor and products recovered down stream of the reactor.

As an alternative to the supply of reducing equivalents by means of a conventional electrochemical cell, the required reducing equivalents may be supplied electrochemically from molecular hydrogen. For example, in a heterogeneous system molecular hydrogen is passed into a secondary solution in which the reaction $H_2 \rightarrow 2H^+ + 2e$ occurs e.g. a solution containing a hydrogenase. This solution contains an electrode e.g. a platinised platinum electrode, which is electrically connected to a second electrode immersed in a primary solution containing the enzymatic reaction system. Electrons supplied by the reaction of molecular hydrogen in the secondary solution are passed to an enzyme in the primary solution enabling the enzyme to interact with substrate e.g. methane and molecular oxygen.

The invention is further described by way of illustration only in the following examples.

EXAMPLE 1

The electrochemical/enzymatic oxidation of methane to methanol is carried out in an electrochemical cell using a crude enzyme extract of *Methylosinus trichosporium*.

The electrochemical cell used consists of two compartments, a working compartment and an auxiliary compartment, separated from one another by a Vycor (Corning Inc.) glass membrane. The working compartment contains a gold foil working electrode of surface area approximately 9 cm$^2$, and in close proximity a standard calomel reference electrode the tip of which is within 1 mm of the gold electrode. A graphite rod anode is situated in the auxiliary compartment, and both compartments contain potassium phosphate as electrolyte. The potential of the working electrode relative to the standard calomel electrode is controlled by a Princeton Applied Research potentiostat model 173.

A crude cell-free extract of methane-grown *Methylosinus trichosporium* is prepared as described by Tonge, Harrison and Higgins (Biochemical Journal, 161, (1977), 333–344). 9.5 ml of the extract containing 85 mg. of protein is introduced to the working compartment of the electrochemical cell together with a few crystals of cupric chloride and 4,4'-bipyridyl (5 mM). The potentiostat is set to maintain the potential of the working electrode relative to the standard calomel electrode at −0.1 V vs. the normal hydrogen electrode. The contents of the electrochemical cell are incubated at room temperature, and magnetically stirred, whilst methane/air mixture (1:1 v/v) is bubbled through the working compartment. After about 90 minutes, at which point about 0.1 coulomb of electricity has passed through the cell, the electric current and gas flow are switched off and the contents of the working compartment are assayed for methanol produced from the methane. The concentration of methanol in the mixture is found to be 60 μm. It was also found that the oxidation of methane to methanol was inhibited by carbon monoxide and cyanide, both of which are known inhibitors of the methane mono-oxygenase of *Methylosinus trichosporium*.

The methane mono-oxygenase system of this organism is known to have a very broad substrate specificity, as described by Higgins et al. (Society of General Microbiology Quarterly, 6, 71, 1979), being capable of oxidising higher alkanes, alkenes and even cyclic organic compounds. It is to be expected, therefore, that such other compounds will be oxidised electroenzymologically substantially as described above. Also the mono-oxygenase enzyme system of *Methylosinus trichosporium* is broadly similar to the enzyme systems of other methane mono-oxygenase organisms, such as *Methylococcus capsulatus*, and thus enzyme systems from methane mono-oxygenase organisms in general may be utilised in similar electroenzymological oxidations.

EXAMPLE 2

Camphor is oxidised to 5-exo-hydroxy-camphor using the camphor mono-oxygenase complex of *Pseudomonas putida*, the reducing equivalents required to drive the reaction being supplied electrochemically directly to the enzyme. The enzyme complex which consists of cytochrome $P_{450\,cam}$ putidaredoxin and putidaredoxin reductase, is isolated from *Pseudomonas putida* strain PpG 786 using the procedures of Gunsalus and Wagner (Methods in Enzymology, 52, 166–188, 1978) excpept that bacterial disruption is modified by use of the lysozyme-EDTA method of O'Keefe et al. (Methods in Enzymology, 52, 151–157, 1978). Investigation of the DC and AC voltammetry of the complex, coupled with spectroelectrochemical measurements indicate that the complex is reduced, in the presence of camphor, at a gold electrode at −700 mV vs S.C.E.

The oxidation of camphor is carried out in a two compartment electrochemical cell fitted with a gold gauze working electrode, a platinum wire counter electrode, and a standard calomel reference electrode mounted in the working compartment of the cell in close proximity to the working electrode. The counter electrode is separated from the working electrode compartment by dialysis tubing.

The reaction solution contained in the working compartment of the cell contains putidaredoxin (10 mg), reductase (2 mg) and cytochrome P-450 (24 nanomoles) in 5.4 ml of Tris (0.05 M), K Cl (0.1 M) buffer at pH 7.4, and is saturated with camphor. The reaction is carried out at 28° C. with a preferred applied potential of −800 mV vs S.C.E. No 5-exo-hydroxycamphor is detected at zero time but the concentration of this compound steadily increases with time, the presence of this product in the reaction mixture being determined by ether extraction of samples followed by analysis by gas liquid chromatography. Using partially purified enzyme (∼30% pure) the yield of hydroxy camphor obtained is of the order of 80 n mol/mg of protein/min.

Comparison of the results obtained with the same reaction driven by the "natural" electron donor, NADH, indicate that in the electroenzymological application the rate of production of the product proceeds at a rate of about one third of that obtained with the "natural" system. It is envisaged, however, that modification of the cell design to optimise the mass transport should give rise to a more comparable rate of product formation.

An experiment carried out at a working electrode potential of −600 mV vs S.C.E. gives a much reduced rate of product formation, approximately one fifth of that observed in the earlier experiment, indicating that reduction of the enzyme at the electrode surface is the rate determining step. A further experiment carried out in the absence of the enzyme complex gives no product formation.

EXAMPLE 3

Luciferase, a flavoprotein enzyme which catalyses the reaction NADH+FMN+aldehyde+$O_2$→light+products, is investigated in a system in which the reducing equivalents required for the enzyme reaction are supplied electrochemically directly to the enzyme. The luciferase used is obtained from *Vibrio Fisheri* as supplied by Sigma Chemical Co., and identified as Type II Cat. No. 2379.

The luciferase reactions are carried out in an electrochemical cell sited adjacent to a photomultiplier tube of an Aminco photometer which is used to measure the light emitted during the reaction. The electrochemical cell used comprises two compartments, a working compartment containing the reaction mixture and a gold gauze working electrode, and an auxiliary compartment separated from the working compartment by dialysis tubing and containing a platinum wire counter electrode. The reaction mixture contains luciferase (7 mg), decyl aldehyde (0.05 ml) and phosphate buffer (1.5 ml at pH 7.0) being made up to a total volume of 8 ml. A standard calomel reference electrode is sited in the working compartment close to the working electrode and all three electrodes are appropriately connected to a Chemical Electronics potentiostat. The applied potential is arranged such that the working electrode is initially set at a potential of 0.0 V vs the S.C.E., after which the potential is gradually maade more negative. When the potential reaches −700 mV the photometer indicates that light is being emitted by the reaction mixture, and the amount of light emitted increases as the potential is made more negative. The most negative potential used being −900 mv. As the potential is made more positive the amount of light emitted decreases.

tein materials provide biologically active carrier materials for transferring reducing equivalents to enzymes.

| Protein | Source | Electrode | Oxidation/Reduction Potential (vs N.H.E.) | Comments |
|---|---|---|---|---|
| Cytochrome c | Horse Heart | Gold/Bipyridyl | +250 mV | Reversible |
| Cytochrome c | Yeast | Gold/Bipyridyl | +250 mV | Reversible |
| Cytochrome c oxidase | Beef Heart mitochondria | Gold | +240 mV | Reversible |
| Cytochrome P450/ cytochrome P450 reductase/ putidaredoxin complex | P. putida | Gold | −520 mV | Reversible; camphor present |
| Cytochrome C3 | D. vulgaris (Norway) | Mercury | −280 mV | Reversible |
| Laccase | Rhusvernicifera | Gold/Bipyridyl | +360 mV | Not quite reversible |
| Ceruloplasmin | Human Blood | Gold/Bipyridyl | +500 mV +600 mV | No quite reversible |
| Superoxide dismutase | Bovine erythrocytes | Gold/Bipyridyl | +440 mV | Not quite reversible |
| Ferredoxin | Cucurbita pepo | Mercury | −355 mV | Reversible |
| Ferredoxin | Spinach | Mercury | −320 mV | Reversible |

The potential is cycled several times between OV and −900 mV, and each time light is emitted at potentials more negative than 700 mV thereby showing that the catalysis by the enzyme depended on the tranfer of electrons from the electrode to the enzyme.

EXAMPLE 4

As alternatively to the supply of reducing equivalents required to drive the enzyme reaction from a conventional electrochemical cell, the reducing equivalents are supplied electrochemically from molecular hydrogen in a heterogeneous system.

The system used comprises two compartments separated by a glass frit membrane, one compartment containing a Johnson Matthey platinum fuel cell electrode (5 mm×15 mm) maintained in phosphate buffer solution (pH 7) containing sodium perchlorate (0.01 M). The other compartment of the system contains a gold net working electrode (10 mm×5 mm) immersed in the same solution, though containing in addition cytochrome c (5 mg/ml) and 4,4-bipyridyl (10 mM). The electrodes in the two compartments are provided with means for electrical connection between them, and the open circuit potential is found to be 630 mV, that which is expected from the reduction potential of cytochrome c. This potential is reversed by passing hydrogen gas into the platinum electrode compartment where the hydrogen relinquishes electrons to the platinum electrode which are then passed on to the cytochrome c via the gold net electrode, the hydrogen combining with oxygen to give water. The reduced form of cytochrome c in the gold electrode compartment is then able to interact with cytochrome oxidase and molecule oxygen to drive the oxidation reactions of this latter enzyme e.g. oxidation of methane to methanol.

EXAMPLE 5

The electrochemical reduction of various biologically active electron donor materials, enzyme complexes and components thereof is carried out in a two compartment cell fitted with a platinum counter electrode as described in previous examples. The results obtaind are given in the table below indicating the proteins which are electrochemically reduced, their sources, the working electrodes used in each case, their oxidation/reduction potentials (vs the NHE) and comments on th reversibility of the reductions. These pro-

We claim:

1. A process for carrying out an enzymatic reaction, which comprises:
continuously supplying reducing equivalents to regenerate a reduce enzyme species in enzymatically active form, said reducing equivalents being derived electrochemically and passed directly to said enzyme from the cathode of an electrochemical system and taken-up and utilized by an electron receptor component of said enzyme.

2. A process for the oxidative or reductive transformation of an organic compound, comprising:
said transformation being catalyzed by an enzyme and the enzyme requiring a continuing supply of reducing equivalents to regenerate a reduced enzyme species in enzymatically active form, said reducing equivalents being derived electrochemically and passed directly to the enzyme from the cathode of an electrochemical system and taken-up and utilized by an electron receptor component of the enzyme.

3. The process of claim 1 or 2, wherein the enzyme comprises an external mono-oxygenase, an oxidoreductase, a dehydrogenase, a nitrogenase, a dioxygenase, a luciferase or a hydrogenase.

4. The process of claim 1 or 2, wherein the working electrode of the electrochemical system comprises a material which is inert to the enzyme species which it is desired to regenerate electrochemically and the auxiliary electrode is separated from the working electrode.

5. The process of claim 1 or 2, wherein the working electrode comprises a liquid crystal coated, semi-conductor or hanging mercury drop electrode.

6. The process of claim 1 or 2, wherein the electrolyte contains an electron transfer promoter.

7. The process according to claim 1 or 2, wherein the potential of the working electrode is controlled at or close to the redox potential of the enzyme species which it is desired to reduce.

8. The process of claim 7, wherein control of the potential of the working electrode is facilitated by use of a reference electrode located within the working region of the electrochemical cell.

9. The process of claim 1 or 2, wherein the enzyme is present as a component of a crude cell extract.

10. The process of claim 1 or 2, wherein said reducing equivalents are supplied to a primary solution containing said enzyme species electrochemically by the oxidation of hydrogen in a secondary solution.

11. The process of claim 1 or 2, wherein a hydrocarbon material is oxidized to an alcohol using a monooxygenase enzyme system derived from methane oxidizing bacteria.

12. The process of claim 11, wherein said monooxygenase enzyme is *Methylosinus trichosporium*.

13. The process of claim 1 or 2, wherein camphor is oxidized to hydroxycamphor by an enzyme system derived from *Pseudomonas putida*.

* * * * *